United States Patent
Makino et al.

(10) Patent No.: US 6,357,297 B1
(45) Date of Patent: Mar. 19, 2002

(54) METHOD FOR PREVENTING SHATTERED-RIM FRACTURE IN RAILWAY WHEELS

(75) Inventors: Taizo Makino; Takashi Fujimura, both of Nishinomiya (JP)

(73) Assignee: Sumitomo Metal Industries, Inc. (JP)

( * ) Notice: Subject to any disclaimer, the term of this patent is extended or adjusted under 35 U.S.C. 154(b) by 0 days.

(21) Appl. No.: 09/587,415

(22) Filed: Jun. 1, 2000

(51) Int. Cl.$^7$ ............................................... G01N 29/04
(52) U.S. Cl. ............................. 73/598; 73/146; 73/760; 73/799
(58) Field of Search ........................ 73/570, 146, 760, 73/799, 788, 802, 598

(56) References Cited

U.S. PATENT DOCUMENTS

| | | | |
|---|---|---|---|
| 3,558,876 A | * 1/1971 | Tillmann | 246/246 |
| 3,596,503 A | * 8/1971 | Gay | 73/67.8 |
| 3,983,745 A | * 10/1976 | Juusola | 73/91 |
| 4,042,273 A | 8/1977 | Heller et al. | 295/30 |
| 4,299,128 A | * 11/1981 | Gruber | 73/627 |
| 4,756,194 A | * 7/1988 | Grandpierre et al. | 73/799 |
| 4,781,060 A | * 11/1988 | Berndt | 73/146 |
| 5,793,492 A | * 4/1991 | Vanaki | 356/376 |
| 5,363,702 A | * 11/1994 | Catot et al. | 73/598 |
| 5,899,516 A | 5/1999 | Fujimura et al. | 295/1 |

OTHER PUBLICATIONS

Sen et al., "Influence of Inclusions and Heat Treatment on Fatigue Strength of Wheel and Axle Steel," *Fatigue Design Symposium* (1998).

Danian et al, "The Effects of Cyclic Softening on the Shakedown Limit of Railway Wheel Steel," *International Conference on Mechanical Behaviour of Materials (6$^{th}$)*, Kyoto, Japan (1992).

Bo et al., "Railway Wheel Rim Fatigue Break–Down and Relevant Problem," *12$^{th}$ International Wheelset Congress Proceedings*, Qingdao, China (Sep. 12–25, 1998).

Qian et al., "Fatigue of Railway Wheel and its Damage," *12$^{th}$ International Wheelset Congress Proceedings*, Qingdao, China (Sep. 21–25, 1998).

Marais, "Wheel Failures on Heavy Haul Freight Wheels Due to Subsurface Defects," *12$^{th}$ International Wheelset Congress Proceedings*, Qingdao, China (Sep. 21–25, 1998).

Lixian et al., "Study on Rim Fatigue Crack and Prevention," *12$^{th}$ International Wheelset Congress Proceedings*, Qingdao, China (Sep. 21–25, 1998).

Catot et al., "Contribution to Improve Steel Grades for Wheels for Heavy Freight Traffic," *International Wheelset Congress*, Sydney, Australia (Sep. 27 –Oct. 1, 1992).

Sakamoto et al., "Simulation Test on Tread Shelling of Railroad Wheel," *Rail Transportation, 12*, pp. 73–78 (1996).

Ekberg et al., "Effects of Imperfections on Fatigue Initiation in Railway Wheels," *Charmec* (Oct. 21, 1999).

Gordon et al., "Evaluation of Service–Induced residual Stresses in Railroad Commuter Car Wheels," *Rail Transportation 15*, pp. 25–31 (1998).

(List continued on next page.)

*Primary Examiner*—Hezron Williams
*Assistant Examiner*—Jacques Saint-Surin
(74) *Attorney, Agent, or Firm*—Leydig, Voit & Mayer, Ltd.

(57) ABSTRACT

A method for easily and effectively preventing shattered-rim fracture in a railway wheel. Generally, the method comprises the steps of providing a railway wheel, measuring the maximum defect size within the rim of the railway wheel, and determining whether the maximum defect size is less than a predetermined maximum permissible defect size, the maximum permissible defect size being determined based on an analysis of the likelihood of Mode II crack propagation from the defect when the railway wheel has been subjected to the load. The disclosed invention also encompasses a method for grading railway wheels for maximum load suitability.

19 Claims, 2 Drawing Sheets

OTHER PUBLICATIONS

Magel et al., "Controlling Wheel Shelling," *Railway Track & Structures* (Nov. 1997).

Synder, "Shattered Rim Update," *Lab Notes* (Jul. 1998).

Diener et al., "Fractures Toughness of R7 Railroad Wheels," *La Metallurgia Italiana, 85* (3), pp. 161–167 (1993).

Sakamoto et al., "Fracture Toughness of Medium–High Carbon Steel for Railroad Wheels," *NSF–IMM Symposium on Micromechanic Modeling of Industrial Materials: In Honor of Professor T. Mori's 65th Birthday*, Seattle, Washington (Jul. 20–22, 1998).

Stone et al., "Wheel Thermal Damage Limits," *ASME, 1994*, pp. 57–63 (1994).

* cited by examiner

METHOD FOR PREVENTING SHATTERED-RIM FRACTURE IN RAILWAY WHEELS

TECHNICAL FIELD OF THE INVENTION

The invention is in the field of railway wheels and, more particularly, relates to preventing shattered-rim fracture in railway wheels.

BACKGROUND OF THE INVENTION

Recently, railroad transport volume, which is sometimes expressed in terms of railroad freight revenue ton-miles, has been increasing to meet an increasing rail transport demand. As a result, railway cars are hauling ever-heavier average loads. For instance, lightweight aluminum coal cars, which can have maximum gross loads up to 286,000 lbs., have become increasingly common. The wheel loads in such "heavy haul" coal cars are approaching permissible limits, a circumstance which results in lower load safety margins for the wheels of such rail cars.

One serious problem with railway wheels is known as shattered-rim fracture.

Shattered-rim fracture is a phenomenon whereby a rolling contact fatigue crack initiates at an internal defect in the wheel rim subsurface and propagates to ultimately cause substantial damage to the wheel. Left unchecked, the shattered-rim fracture can cause catastrophic failure of the railway wheel and derailment of the rail car. This problem can be exacerbated with increasing wheel speed, unbalanced loads, heavy braking, and other circumstances common in the railway industry.

Given the general increase in freight revenue ton-miles in the rail industry, there is an increasing need to prevent shattered-rim fracture in railway wheels.

OBJECTS AND SUMMARY OF THE INVENTION

It is a general object of the invention to provide a method for preventing catastrophic failure of railway wheels.

Another object of the invention is to provide a method for more effectively preventing shattered-rim fracture in railway wheels.

A further object is to provide a method for testing railway wheels for load suitability during intended usage.

Still another object is to provide a method for grading railway wheels as to load suitability.

Yet another object is to provide methods as characterized above that can be easily and effectively carried out.

Another object is to provide methods of the foregoing types that can be selectively carried out at different safety level rankings.

It is believed that a major cause of the shattered-rim fracture phenomenon is Mode II (in-plane shearing) crack propagation from defects in the rim of the railway wheel. It has now been discovered that shattered-rim fracture in railway wheels can be substantially avoided if the rim of the wheel does not contain defects of a size such as to lead to a Mode II stress intensity factor range ($\Delta K_{II}$) at the maximum intended load that is greater than the threshold Mode II stress intensity factor range ($\Delta K_{IITH}$) required for cracks to propagate from the defect. The invention makes use of this discovery to prevent shattered-rim fracture in railway wheels. In general, the invention contemplates an analysis of the likelihood of Mode II crack propagation from defects in the rim of a railway wheel. Such analysis may be used to determine the suitability of a railway wheel for carrying a maximum intended load, or alternatively, may be used to determine the maximum suitable load for a railway wheel.

In accordance with a highly preferred embodiment of the invention, a method is provided for more efficiently and effectively preventing shattered-rim fracture in a railway wheel. Generally, the method comprises providing a railway wheel that is expected to be subjected to an intended load, measuring the size of the largest defect within the rim of the wheel, and determining whether the defect size of this defect is below a pre-determined maximum permissible defect size for the intended load. The predetermined maximum defect size is ascertained by evaluating the likelihood of crack propagation from the defect upon subjecting the wheel to the intended load. In accordance with another highly preferred embodiment of the invention, the method for preventing shattered-rim fracture generally comprises the steps of measuring the maximum size of defects in the railway wheel rim, and determining the maximum usage load suitable for said wheel based on a predetermined correspondence between permissible load and defect sizes.

Other objects and advantages of the invention will become apparent upon reading the following detailed description and upon reference to the drawings, in which:

Figure 1:
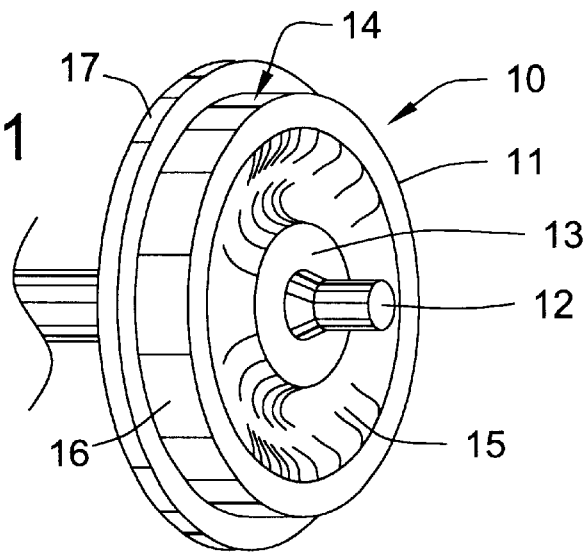
FIG. 1 is a fragmentary perspective view of a railway wheelset that includes a typical railway wheel.

While the invention is susceptible of various modifications and alternative constructions, a certain illustrated embodiment thereof has been shown in the drawings and will be described below in detail. It should be understood, however, that there is no intention to limit the invention to the specific form disclosed but, on the contrary, the intention is to cover all modifications, alternative constructions and equivalents falling within the spirit and scope of the invention.

DETAILED DESCRIPTION OF THE PREFERRED EMBODIMENT

Figure 2:
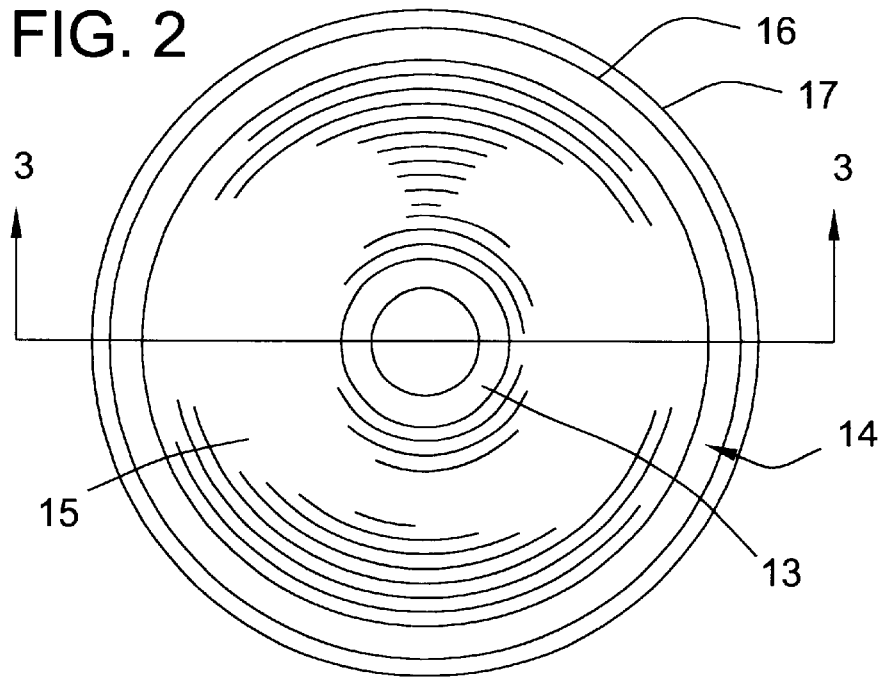
FIG. 2 is a side elevational view of the railway wheel illustrated in FIG. 1.
Figure 3:
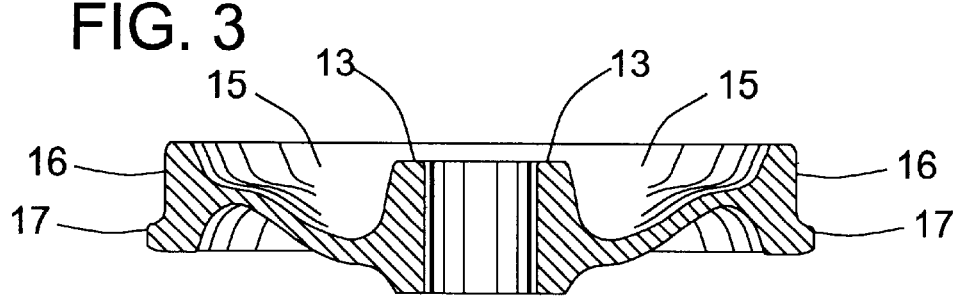
FIG. 3 is a section taken in the plane of line 3—3 in FIG. 2.

The invention is particularly applicable to the analysis of railway wheels of a conventional type. Referring now particularly to FIGS. 1–3, there is shown a portion of an illustrative wheelset 10 that includes a typical railway wheel 11 mounted on an axle 12. The wheel 11 in this instance comprises a hub 13, a rim 14, and a connecting plate 15, with the rim 14 comprising a tread 16 and a flange 17. Shattered-rim fracture in the illustrated wheel would occur when a crack develops in the rim 14.

The likelihood of crack propagation from a defect, such as an internal inclusion, pore, void, vacancy, or the like, may be determined using an analysis of the likelihood of Mode II (in-plane shearing) crack propagation from defects in the rim of the railway wheel. Generally, the Mode II stress intensity factor range ($\Delta K_{II}$) for a defect of a given size can be estimated for a railway wheel for a given wheel diameter and intended wheel load. If the Mode II stress intensity factor range ($\Delta K_{IITH}$) estimated for a given defect in the rim of the railway wheel is greater than the threshold Mode II stress intensity factor range ($\Delta K_{IITH}$) for the wheel rim, then one would expect that cracks would propagate from the defect. If, on the other hand, the Mode II stress intensity factor range ($\Delta K_{II}$) is estimated to be less than the threshold Mode II stress intensity factor range ($\Delta K_{IITH}$), than one would expect that cracks will not propagate from the defect. The maximum permissible defect size thus is found when $$\Delta K_{II} = \Delta K_{IITH}$$

for a given defect size and intended load.

Figure 4:
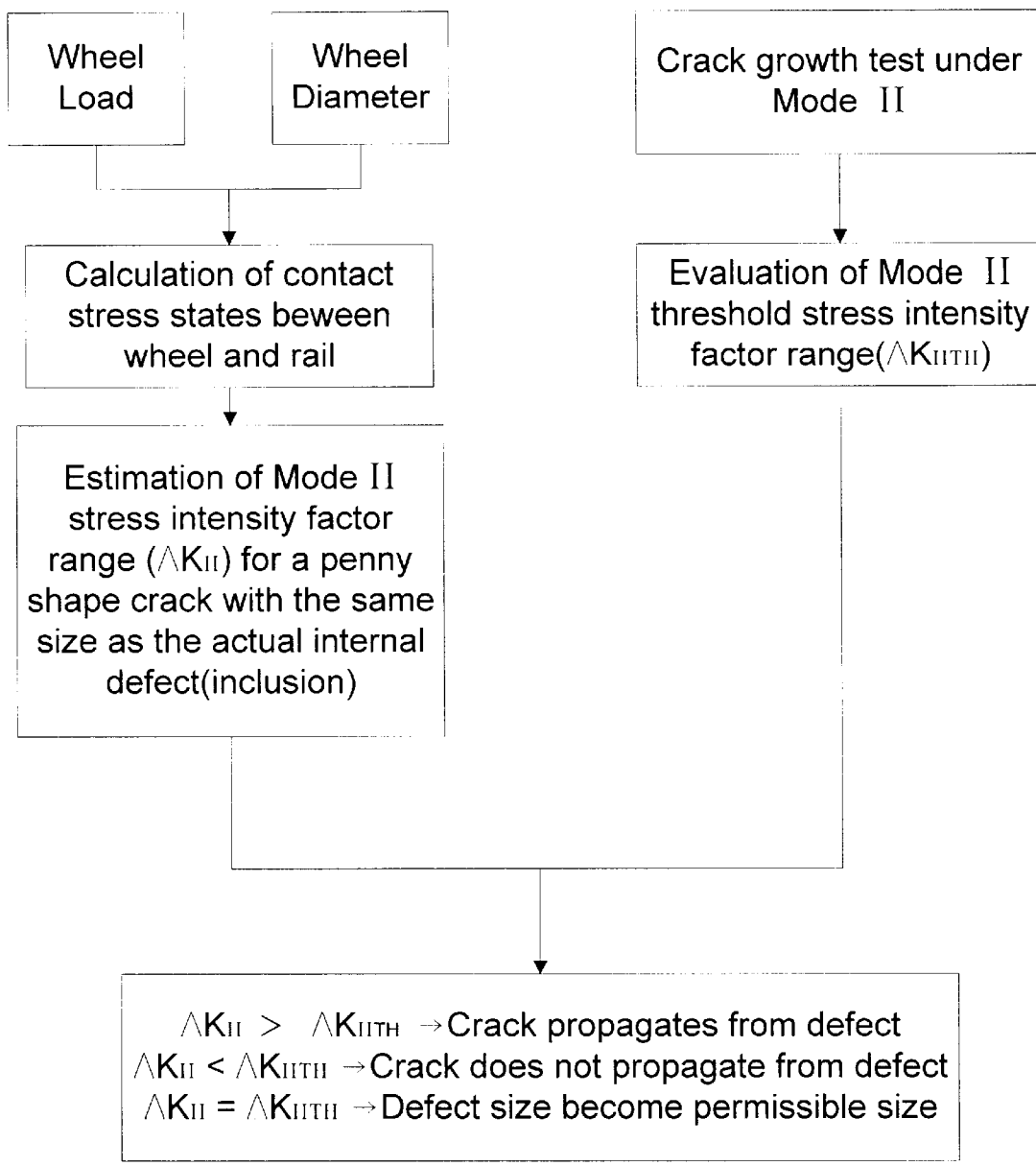
FIG. 4 is a flowchart representing a general Mode II crack propagation analysis for railway wheels.

As illustrated in FIG. 4, one may generally conduct a Mode II crack propagation analysis by calculating the contact stress between the railway wheel and a rail, taking into account the wheel load and wheel diameter. The Mode II stress intensity factor range ($\Delta K_{II}$) then is estimated for the defect in the railway wheel rim. Generally, one may calculate the Mode II stress intensity factor range for a threshold crack having the shape of a penny with a diameter equal to the size of the defect, i.e., diameter of the equivalent flat bottom hole detected ultrasonically. The calculation of the Mode II stress intensity factor range is a standard calculation in the art. Likewise, experimental evaluation of the threshold Mode II stress intensity factor range ($\Delta K_{IITH}$) is a standard procedure in the art. This threshold range may be estimated via crack growth tests, as described, for example, in Hamada et al., "Measurement of Mode II threshold stress intensity factor range ($\Delta K_{IITH}$)," *I.C. M & M '97* (1997) pp. 311–12. Once the Mode II stress intensity factor range ($\Delta K_{II}$) and the threshold Mode II stress intensity factor range ($\Delta K_{II}$) have been determined, the relative magnitude of the stress intensity factor range ($\Delta K_{II}$) can be compared to the magnitude of the threshold Mode II stress intensity factor range ($\Delta K_{IITH}$) to determine the likelihood that a crack will propagate from the defect.

Determination of the foregoing stress intensity factor ranges may be inexact and subject to estimation and, in conducting a Mode II crack propagation analysis, estimates of both the Mode II stress intensity factor range ($\Delta K_{II}$) and the threshold Mode II stress intensity factor range ($\Delta K_{IITH}$) may vary. In particular, empirical estimates of the threshold Mode II stress intensity factor range ($\Delta K_{IITH}$) may vary depending on the level of safety desired, with lower estimates of the threshold Mode II stress intensity factor range corresponding to higher margins of safety. For instance, if plural crack propagation tests are conducted, the minimum, maximum, mean, or other test value may be taken as the threshold Mode II stress intensity factor range estimate. Likewise, estimates of the Mode II stress intensity factor ranges ($\Delta K_{II}$) for defect sizes may vary depending on the level of safety desired, with higher estimates of the Mode II stress intensity factor range corresponding to higher margins of safety.

In practice, the evaluation of load suitability or assignment of a load rating to a railway wheel does not necessarily involve calculation of the stress intensity factor ranges, but more likely is conducted with reference to pre-calculated values. Most preferably, different Mode II stress intensity factor ranges ($\Delta K_{II}$) for different defect sizes may be estimated and a record prepared that correlates defect sizes with permissible loads. One may prepare such a correlation record by determining a plurality of wheel loads that, for a corresponding plurality of defect sizes, would correspond to a Mode II stress intensity factor range that is not greater than the threshold Mode II stress intensity factor range for the wheel rim. In making such determination, either the defect size may be calculated from a predetermined wheel load, or the wheel load may be calculated from a predetermined defect size, and an additional margin of safety may be imposed on the calculated values, if desired. The correlation record thus prepared may be used in conjunction with actual measurements of defects in railway wheels to determine load suitability or to assign load ratings to the wheel.

In light of the foregoing, the invention encompasses the preparation of a table that correlates permissible defect sizes to permissible loads for a given wheel. Such a correlation table may be prepared by estimating defect sizes for wheel loads that will result in Mode II stress intensity factor ranges that are not greater than the threshold Mode II stress intensity factor range, and tabulating the defect sizes and wheel loads. In keeping with this aspect of the invention, two possible correlation records between defect sizes and permissible loads for conventional steel railway wheels of various diameters have been prepared and are set forth hereinbelow.

TABLE 1

Rank I
Safety Level-$\Delta K_{IITH}$ (18 MPa$\sqrt{m}$)

| Wheel Dia. [inch] D | Wheel Load (kN) L | Permissible Defect Size (dia.) [mm] | Wheel Dia. [inch] D | Wheel Load [kN] L | Permissible Defect Size (dia.) [mm] |
|---|---|---|---|---|---|
| 28 < D ≤ 30 | 80 < L ≤ 110 | 1.017 | 34 < D ≤ 36 | 80 < L ≤ 110 | 1.133 |
|  | 110 < L ≤ 140 | 0.854 |  | 110 < L ≤ 140 | 0.969 |
|  | 140 < L ≤ 170 | 0.727 |  | 140 < L ≤ 170 | 0.838 |
|  | 170 < L ≤ 200 | 0.627 |  | 170 < L ≤ 200 | 0.732 |
|  | 200 < L ≤ 230 | 0.546 |  | 200 < L ≤ 230 | 0.645 |
|  | 230 < L ≤ 260 | 0.480 |  | 230 < L ≤ 260 | 0.573 |
| 30 < D ≤ 32 | 80 < L ≤ 110 | 1.057 | 36 < D ≤ 38 | 80 < L ≤ 110 | 1.168 |
|  | 110 < L ≤ 140 | 0.893 |  | 110 < L ≤ 140 | 1.004 |
|  | 140 < L ≤ 170 | 0.765 |  | 140 < L ≤ 170 | 0.873 |
|  | 170 < L ≤ 200 | 0.662 |  | 170 < L ≤ 200 | 0.766 |
|  | 200 < L ≤ 230 | 0.579 |  | 200 < L ≤ 230 | 0.677 |
|  | 230 < L ≤ 260 | 0.510 |  | 230 < L ≤ 260 | 0.603 |
| 32 < D ≤ 34 | 80 < L ≤ 110 | 1.095 | 38 < D ≤ 40 | 80 < L ≤ 110 | 1.201 |
|  | 110 < L ≤ 140 | 0.931 |  | 110 < L ≤ 140 | 1.038 |
|  | 140 < L ≤ 170 | 0.802 |  | 140 < L ≤ 170 | 0.906 |
|  | 170 < L ≤ 200 | 0.697 |  | 170 < L ≤ 200 | 0.798 |
|  | 200 < L ≤ 230 | 0.612 |  | 200 < L ≤ 230 | 0.708 |
|  | 230 < L ≤ 270 | 0.542 |  | 230 < L ≤ 260 | 0.632 |

TABLE II

Rank II
Acceptable Safety Level-$\Delta K_{IITH}$ = 20 MPa√m)

| Wheel Dia. [inch] D | Wheel Load (kN) L | Permissible Defect Size (dia.) [mm] | Wheel Dia. [inch] D | Wheel Load [kN] L | Permissible Defect Size (dia.) [mm] |
|---|---|---|---|---|---|
| 28 < D ≤ 30 | 80 < L ≤ 110 | 1.256 | 34 < D ≤ 36 | 80 < L ≤ 110 | 1.398 |
| | 110 < L ≤ 140 | 1.054 | | 110 < L ≤ 140 | 1.196 |
| | 140 < L ≤ 170 | 0.898 | | 140 < L ≤ 170 | 1.035 |
| | 170 < L ≤ 200 | 0.774 | | 170 < L ≤ 200 | 0.904 |
| | 200 < L ≤ 230 | 0.674 | | 200 < L ≤ 230 | 0.796 |
| | 230 < L ≤ 260 | 0.592 | | 230 < L ≤ 260 | 0.707 |
| 30 < D ≤ 32 | 80 < L ≤ 110 | 1.305 | 36 < D ≤ 38 | 80 < L ≤ 110 | 1.442 |
| | 110 < L ≤ 140 | 1.103 | | 110 < L ≤ 140 | 1.240 |
| | 140 < L ≤ 170 | 0.944 | | 140 < L ≤ 170 | 1.078 |
| | 170 < L ≤ 200 | 0.818 | | 170 < L ≤ 200 | 0.945 |
| | 200 < L ≤ 230 | 0.715 | | 200 < L ≤ 230 | 0.836 |
| | 230 < L ≤ 260 | 0.630 | | 230 < L ≤ 260 | 0.744 |
| 32 < D ≤ 34 | 80 < L ≤ 110 | 1.352 | 38 < D ≤ 40 | 80 < L ≤ 110 | 1.482 |
| | 110 < L ≤ 140 | 1.150 | | 110 < L ≤ 140 | 1.281 |
| | 140 < L ≤ 170 | 0.990 | | 140 < L ≤ 170 | 1.118 |
| | 170 < L ≤ 200 | 0.861 | | 170 < L ≤ 200 | 0.985 |
| | 200 < L ≤ 230 | 0.756 | | 200 < L ≤ 230 | 0.874 |
| | 230 < L ≤ 270 | 0.669 | | 230 < L ≤ 260 | 0.781 |

The "Rank I" Table represents a safety level for railway wheels in which the threshold Mode II intensity factor range was estimated as having a value of 18 MPa√m, and wherein this estimated value for $\Delta K_{IITH}$ was used to derive maximum permissible defect sizes. The Rank II Table represents an acceptable safety level in which an estimated threshold Mode II stress intensity factor range ($\Delta K_{IITH}$) of 20 MPa√m was used to derive maximum permissible defect sizes. These values were estimated based on empirical crack propagation tests, with 18 MPa√m being the mean test result and 20 MPa√m being the maximum. In keeping with this aspect of the invention, the user may select the safety level or the acceptable safety level.

In carrying out the invention, the foregoing Tables may be used in determining the maximum permissible defect size in railway wheel rims. The size of an actual defect in a given railway wheel rim can be compared to the maximum permissible defect size expressed in one of the foregoing Tables for a given intended load. Generally, the largest defect in the rim should be measured, with the size of the defect preferably being measured ultrasonically in accordance with known techniques. If the maximum defect size is below the maximum permissible defect size for the intended load, then the railway wheel will be deemed suitable for the intended load; otherwise, the railway wheel will be deemed unsuitable for the intended load. For instance, using the Rank II Table, if the intended wheel load for a 30 inch wheel is 185 kN, and if the maximum defect size in the wheel is found to be 0.800 mm, the wheel may be deemed unsuitable for use with the intended load. On the other hand, if the maximum intended load for the wheel is 100 kN, the wheel may be deemed suitable for use with the intended load.

In carrying out a further aspect of the invention, a method is provided for the assignment of load ratings to railway wheels. To this end, the defect size measured in the rim of the railway wheel may be compared to the maximum permissible defect size in the Rank I or Rank II Table to determine the maximum load suitability for the wheel. For instance, using the Rank II Table, if the maximum defect size in a given 30 inch wheel is found to be 0.800 mm, then the maximum wheel load should be no more than 170 kN and the wheel may be assigned this load rating. The wheel should be deemed unsuitable for carrying greater loads, inasmuch as the maximum permissible defect size for greater loads is 0.774 mm, which is exceeded by the actual size of at least one defect in the wheel. Again, one may choose values from the Rank II Table if a lower safety level is deemed acceptable, or instead from the Rank I Table if a higher safety level is deemed necessary.

The utility of the Rank I and Rank II Tables in predicting shattered-rim fracture may be confirmed by referring to real railway wheels. For example, an actual railway wheel that failed due to shattered-rim fracture is reported in Marais, "Wheel Fractures in Heavy Haul Freight Wheels Due to Substance Defects," *Twelfth International Wheelset Congress* (1998) pp. 306–13. The fracture in this wheel was found to have originated from an inclusion in the rim of the wheel. The wheel load was 130 kN at the time of fracture, the diameter of the wheel was 34.24 inches (870 mm), and the inclusion size at the origin of the fracture was approximately 1.0 mm. Referring to the Rank I and Rank II Tables, it is seen that the maximum permissible defect size for this wheel under this load is 0.969 mm (referring to the Rank I Table) and 1.196 mm (referring to the Rank II Table). It is thus seen that the defect in the rim was close to or exceeded the estimated maximum defect size permissible for the wheel rim. The defect was greater than that deemed permissible according to the Rank I Table. While the defect was within the permissible range according to the Rank II Table, the Rank II Table may be deemed useful as an aid in estimating permissible defect sizes.

Of course, those skilled in the art may make other estimates of the threshold Mode II stress intensity factor range for the particular railway wheel being evaluated. Those skilled in the art also may evaluate or empirically determine other permissible loads or permissible defect sizes for a given load. Accordingly, the specific Rank I and Rank II Tables should be regarded as exemplary of broader aspects of the invention.

From the foregoing, it can be seen that the invention provides a method for effectively preventing catastrophic failure of railway wheels due to shattered-rim fracture. With empirical tables developed for desired safety levels, the method can be quickly and efficiently carried out. The methods of the invention further may be employed to easily test and assign load ratings to railway wheels.

What is claimed is:

1. A method for preventing shattered-rim fracture in a railway wheel, comprising the steps of:

measuring the size of the largest internal defect in said rim;

determining the maximum permissible load for said wheel by comparing said measured largest defect size with a predetermined correlation of defect sizes to permissible loads for said railway wheel; and wherein said predetermined correlation has been obtained by determining a plurality of wheel loads that, for a corresponding plurality of defect sizes, would correspond to a Mode II stress intensity factor range that is not greater than an estimated threshold Mode II stress intensity factor range for said wheel rim.

2. A method according to claim 1, including the steps of providing a maximum intended load for said wheel, and rejecting said wheel for usage if said maximum permissible load is less than the provided maximum intended load.

3. A method according to claim 2, including the step of making said predetermined correlation of defect sizes to permissible loads by determining a plurality of wheel loads that, for a corresponding plurality of defect sizes, would correspond to a Mode II stress intensity factor range that is not greater than an estimated threshold Mode II stress intensity factor range for said wheel rim.

4. A method according to claim 3, including the step of estimating the threshold Mode II stress intensity factor range for said wheel rim.

5. A method for preventing shattered-rim fracture in a railway wheel, comprising the steps of:

measuring the size of the largest internal defect in said rim;

determining the maximum permissible load for said wheel by comparing said measured largest defect size with a predetermined correlation of defect sizes to permissible loads for said railway wheel; and making said predetermined correlation of defect sizes to permissible loads by determining a plurality of wheel loads that, for a corresponding plurality of defect sizes, would correspond to a Mode II stress intensity factor range that is not greater than an estimated threshold Mode II stress intensity factor range for said wheel rim.

6. A method for preventing shattered-rim fracture in a railway wheel, comprising the steps of:

measuring the size of the largest internal defect in said rim;

determining the maximum permissible load for said wheel by comparing said measured largest defect size with a predetermined correlation of defect sizes to permissible loads for said railway wheel;

estimating the threshold Mode II stress intensity factor range for said wheel rim; and making said predetermined correlation of defect sizes to permissible loads by determining a plurality of wheel loads that, for a corresponding plurality of defect sizes, would correspond to a Mode II stress intensity factor range that is not greater than an estimated threshold Mode II stress intensity factor range for said wheel rim.

7. A method for preventing shattered-rim fracture in a railway wheel, comprising the steps of:

measuring the size of the largest internal defect in said rim;

determining the maximum permissible load for said wheel by comparing said measured largest defect size with a predetermined correlation of defect sizes to permissible loads for said railway wheel; and assigning a load rating to said wheel that is not greater than said maximum permissible load;

wherein said predetermined correlation has been obtained by determining a plurality of wheel loads that, for a corresponding plurality of defect sizes, would correspond to a Mode II stress intensity factor range that is not greater than an estimated threshold Mode II stress intensity factor range for said wheel rim.

8. A method according to claim 7, further including the step of making said predetermined correlation of defect sizes to permissible loads by determining a plurality of wheel loads that, for a corresponding plurality of defect sizes, would correspond to a Mode II stress intensity factor range that is not greater than an estimated threshold Mode II stress intensity factor range for said wheel rim.

9. A method according to claim 8, further including the step of: estimating the threshold Mode II stress intensity factor range for said wheel rim.

10. A method for preventing shattered-rim fracture in a railway wheel that in service is expected to be subjected to a maximum intended load, comprising the steps in any appropriate order of:

providing a railway wheel having a rim, a hub, and a plate connecting said rim to said hub;

measuring the size of the largest internal defect in said rim;

estimating the Mode II stress intensity factor range for said largest defect when said wheel is subjected to said maximum intended load;

determining whether a crack is likely to propagate from said defect by comparing the magnitude of said Mode II stress intensity factor range to an estimated threshold Mode II stress intensity factor range for said wheel; and rejecting said wheel if it is determined that a crack is likely to propagate from said defect when said wheel is subject to said maximum intended load.

11. A method according to claim 10, including estimating said Mode II stress intensity factor range by evaluating the contact stress between said wheel and a rail when said wheel is subjected to said maximum intended load.

12. A method for assigning a load rating to a railway wheel, comprising the steps of:

providing a railway wheel having a rim, a hub, and a plate connecting said rim to said hub;

measuring the size of the largest internal defect in said rim;

estimating the largest load that corresponds to a Mode II stress intensity factor range for said largest defect that is not greater than the threshold Mode II stress intensity factor range for said wheel rim;

and assigning said wheel a load rating not greater than said largest load.

13. A method for preventing shattered-rim fracture in a railway wheel that in service is expected to be subjected to a maximum intended load, comprising the steps in any appropriate order of:

providing a railway wheel having a rim, a hub, and a connecting plate between the rim and the hub;

calculating a maximum defect size for said maximum intended load by determining the maximum defect size that corresponds to a Mode II stress intensity factor range that is not greater than an estimated threshold Mode II stress intensity factor range for said wheel rim;

measuring the size of the largest defect within said rim;

and rejecting said wheel for usage if said size of said largest defect is greater than said maximum permissible defect size.

14. A method for assigning a load rating to a railway wheel, comprising the steps of:

providing a railway wheel having a rim, a hub, and a connecting plate between said rim and said hub;

measuring the size of the largest defect within said rim;

calculating a maximum permissible load for said wheel by determining the load that for said size of said largest defect corresponds to a Mode II stress intensity factor range that is not greater than an estimated threshold Mode II stress intensity factor range for said railway wheel rim; and assigning a load rating to said railway wheel not greater than said maximum permissible load.

15. A method for preventing shattered-rim fracture in a railway wheel that in service is expected to be subjected to a maximum intended load, the method comprising the steps in any appropriate order of:

providing a railway wheel, said wheel comprising a wheel, a hub, and a connecting plate between said rim and said hub;

estimating the threshold Mode II stress intensity factor range for said railway wheel rim;

measuring the size of the largest defect within said rim;

estimating the Mode II stress intensity factor range for said defect for said maximum intended wheel load;

comparing said Mode II stress intensity factor range to said threshold Mode II stress intensity factor range; and evaluating said wheel as being suitable or unsuitable for said intended load based on the relative magnitude of said Mode II stress intensity factor range and said threshold Mode II stress intensity factor range.

16. A method for preventing shattered-rim fracture in a railway wheel, comprising the steps in any appropriate order of:

providing a railway wheel, said wheel comprising a wheel, a hub, and a connecting plate between said rim and said hub, estimating the threshold Mode II stress intensity factor range for said wheel rim;

measuring the size of the largest defect within said rim;

estimating the maximum permissible load that corresponds to a Mode II stress intensity factor range for said defect that is not greater than said threshold Mode II stress intensity factor range for said wheel; and assigning said wheel a load rating not greater than said maximum permissible load.

17. A method for preparing a correlation table for use in preventing shattered-rim fracture, comprising the steps of:

estimating a first defect size in a railway wheel a first maximum wheel load that results in a Mode II stress intensity factor range that is not greater than an estimated threshold Mode II stress intensity factor range for said wheel rim;

estimating for a second defect size in a railway wheel a second maximum wheel load that results in a Mode II stress intensity factor range that is not greater than said estimated threshold Mode II stress intensity factor range for said wheel rim; and tabulating said first and second defect sizes with said first and second wheel loads.

18. A method for evaluating a railway wheel that, in service, is expected to be subjected to a maximum intended load, comprising the steps of:

providing a railway wheel, said wheel comprising a rim, a hub, and a plate connecting said rim to said hub; and estimating a maximum permissible defect size that for said maximum intended load would correspond to a Mode II stress intensity factor range that is not greater than an estimated threshold Mode II stress intensity factor range for said wheel rim.

19. A method according to claim 18, further comprising the step of rejecting said wheel if said rim has a defect having a size that is greater than said maximum permissible defect size.

* * * * *

UNITED STATES PATENT AND TRADEMARK OFFICE
CERTIFICATE OF CORRECTION

PATENT NO. : 6,357,297 B1  Page 1 of 1
DATED : March 19, 2002
INVENTOR(S) : Makino et al.

It is certified that error appears in the above-identified patent and that said Letters Patent is hereby corrected as shown below:

Column 2,
Line 66, "$K_{IITH}$" should read -- $K_{II}$ --

Column 7,
Line 10, "wheel, and rejecting" should read -- wheel, rejecting --

Signed and Sealed this

Fourth Day of June, 2002

Attest:

JAMES E. ROGAN
Attesting Officer    Director of the United States Patent and Trademark Office